United States Patent [19]

Jensen et al.

[11] Patent Number: 5,697,938
[45] Date of Patent: Dec. 16, 1997

[54] DEVICE FOR SQUEEZING AND CUTTING AN UMBILICAL CORD

[75] Inventors: Knud Lykke Jensen, Kvistgård; Per Baunsgaard, Hedehusene, both of Denmark

[73] Assignee: Price Invena ApS, Horsholm, Denmark

[21] Appl. No.: 618,357

[22] Filed: Mar. 19, 1996

Related U.S. Application Data

[63] Continuation of PCT/DK94/00364, filed Sep. 30, 1994.

[30] Foreign Application Priority Data

Sep. 30, 1993 [DK] Denmark ................ 1101/93

[51] Int. Cl.$^6$ ................ A61B 17/42; A61B 17/46
[52] U.S. Cl. ................ 606/120; 606/151; 30/272.1
[58] Field of Search ................ 606/120, 158, 606/151, 174; 30/134, 90.6, 90.7, 162, 272.1, 124, 692

[56] References Cited

U.S. PATENT DOCUMENTS

| | | |
|---|---|---|
| 2,524,337 | 10/1950 | Whittaker .................. 606/120 |
| 3,631,858 | 1/1972 | Ersek ...................... 606/174 |
| 4,428,374 | 1/1984 | Auburn .................... 606/120 |
| 4,557,049 | 12/1985 | Cribbs et al. ............. 30/124 |
| 4,716,886 | 1/1988 | Schulman et al. .......... 606/120 |
| 4,781,188 | 11/1988 | Collins .................... 606/120 |
| 4,831,734 | 5/1989 | De Ruyter et al. ......... 30/124 |
| 4,856,517 | 8/1989 | Collins et al. ............ 606/120 |
| 4,938,215 | 7/1990 | Schulman et al. .......... 606/120 |
| 5,018,275 | 5/1991 | Huang ..................... 30/124 |
| 5,462,555 | 10/1995 | Bolanos et al. ............ 606/120 |

FOREIGN PATENT DOCUMENTS

| | | | |
|---|---|---|---|
| 927085 | 5/1973 | Canada ........... | 30/272.1 |
| 8504091 | 9/1985 | WIPO . | |
| 8706449 | 11/1987 | WIPO . | |
| 8905125 | 6/1989 | WIPO . | |

Primary Examiner—Robert A. Hafer
Assistant Examiner—Justine R. Yu
Attorney, Agent, or Firm—Jacobson, Price, Holman & Stern, PLLC

[57] ABSTRACT

An improved disposable device for squeezing and cutting an umbilical cord comprising at least one clamp (1) having two legs interconnected by a hinge, said legs being supported in recesses of a holder (5). The holder further includes a knife (8). The umbilical cord is squeezed and cut when the holder is shifted along the clamp.

10 Claims, 3 Drawing Sheets

DEVICE FOR SQUEEZING AND CUTTING AN UMBILICAL CORD

This is a continuation application on PCT/DK94/00364 designating the U.S., presently pending, entitled "A device for clamping and cutting e.g. an umbilical cord," and filed on Sep. 30, 1994, by the same inventors.

BACKGROUND OF THE INVENTION

1. Field of the Invention

The present invention relates to a device for squeezing and cutting an umbilical cord, and the device has at least one clamp with two legs interconnected by a hinge at one end of the clamp, and a holder by means of which the clamp can be closed. The holder has a knife cutting the umbilical cord after it has been squeezed by the clamp.

2. General Background

U.S. Pat. No. 4,856,517 relates to such a device where the holder consists of a lower part and an upper part interconnected by a hinge. The holder has two grooves into which two open clamps can be inserted. When the holder closes on an umbilical cord, the clamps are also closed. The holder and the clamps are locked in the end position. After the umbilical cord has thus been squeezed in two places, it is cut by a slide and knife being shifted on the holder between the two clamps. The locking mechanism of the holder is then released, and the two squeezed parts of the umbilical cord can be released from the holder.

Because of the two-piece holder and the separate slide this prior art device is very complicated to make. An when the holder is opened after an umbilical cord has been cut, the knife is exposed which has to be considered very unfortunate from a safety point of view.

SUMMARY OF THE INVENTION

The objective of the invention is to provide an improved device of the said kind but without the above-mentioned disadvantages. The device of the present invention is simpler to make (fewer parts and simpler shapes), and the knife is placed so that it is always inaccessible. According to the Danish Working Environment Service, inaccessibility means that no access to the knife has an opening larger than approximately 6 mm.

According to the invention this is achieved by the holder being provided with a through-going bore of a design allowing the hinged end of the clamp to be inserted in the bore and of a size allowing the holder to be moved along the legs of the clamp so that the clamp is closed and the knife of the holder is stationary and placed in such a way that the umbilical cord is cut when the clamp is closed and the holder is shifted further along the legs of the clamp.

To cut an umbilical cord, two clamps are normally used, and according to the invention it is, therefore, expedient that the holder should have a second identical bore, in parallel with the first-mentioned bore, for a second identical clamp and that the knife should be placed between the two bores.

In the said device, the knife is stationary inside the holder so that it will not be accessible even after cutting an umbilical cord. And the holder is constituted e.g. by a die cast part without a separate slide. The entire device thus consists of a holer and one or two clamps.

According to the invention is expedient that the second clamp should have a catch at the free end of the legs for locking the clamp in the closed position, and that the second bore should open outwards and be equipped with blocking devices which interact with corresponding devices on the second clamp in order that the second clamp can be withdrawn through the opening when the holder is shifted past the position in which the clamp is locked and the umbilical cord is cut. When the umbilical cord has been cut, the second locked clamp can then be separated easily from the holder which is still locking the first clamp.

DETAILED DESCRIPTION OF THE PREFERRED EMBODIMENT

Figure 1:
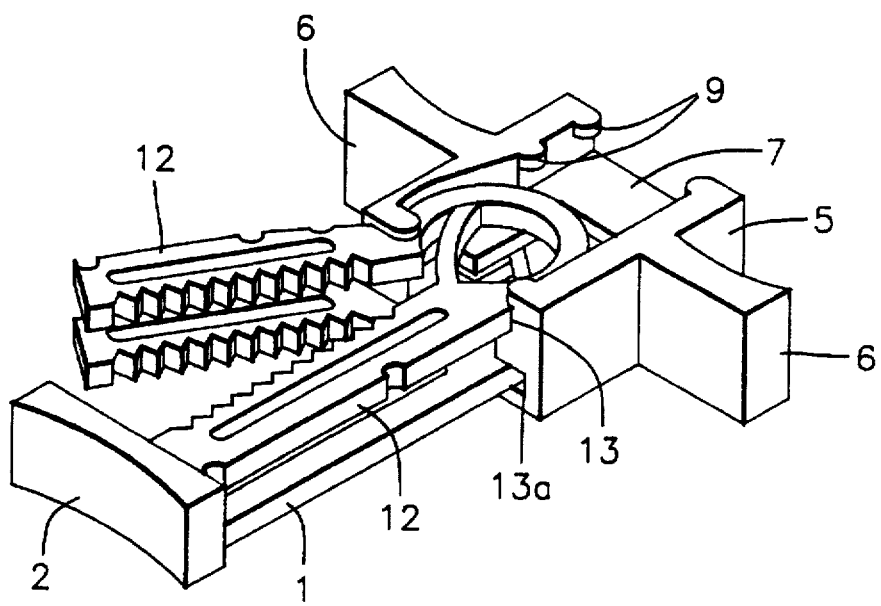
FIG. 1 is a perspective of the disposable safety squeezing device in the open position, with two clamps of which the control clamp faces downward.
Figure 2:
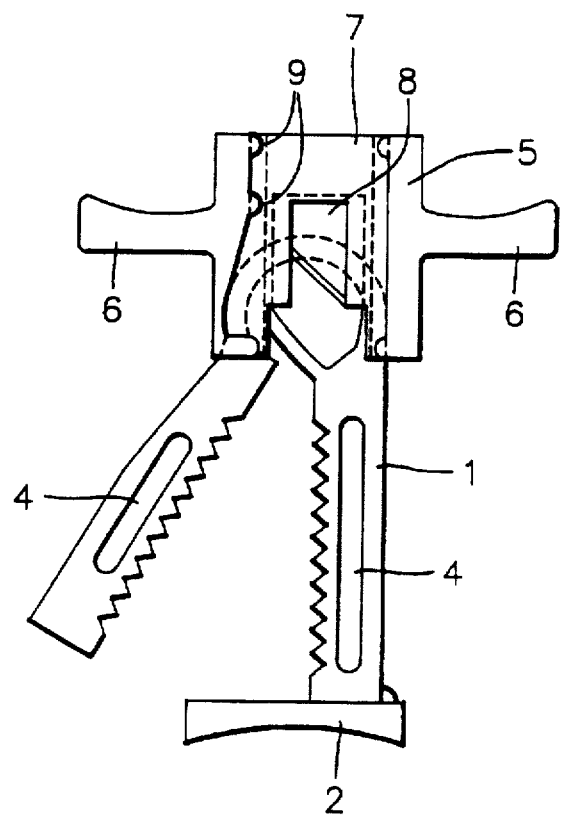
FIG. 2 is a side view of the disposable squeezing device in the open position and with the control clamp mounted.
Figure 3:
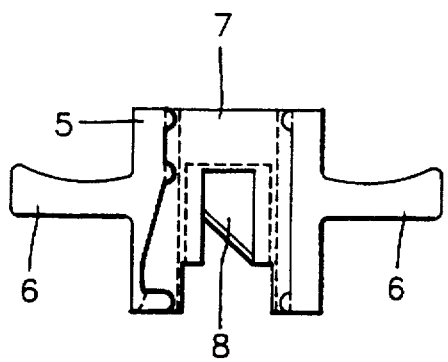
FIG. 3 is a side view of the holder seen from one side.

FIG. 1 shows a disposable double squeezing device with a control clamp 1 and a second clamp 12.

The hinge ends of the control clamp 1 and the second clamp 12 are pushed into through-going bores or grooves 13 and 13a in the holder 5.

The holder 5 has two control tabs 6 and a partition 7 between the two grooves 13 and 13a. An inclined knife 8 is mounted in the partition 7.

Clamps 1 and 12 are secured in one direction in grooves 13 and 13a of the holder by their initial tension. In the opposite direction, at right angles to the first-mentioned direction, the control clamp 1 is secured by the outer wall 14 which closes the groove 13a, and some projections 9 which close the groove 13 for the second clamp 12.

Figure 4:
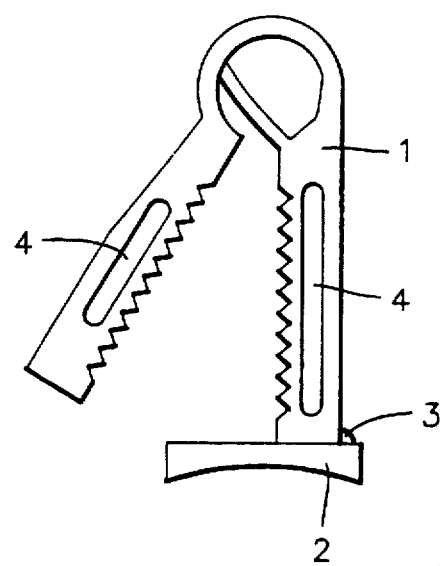
FIG. 4 is a side view of the control clamp in the open position.
Figure 5:
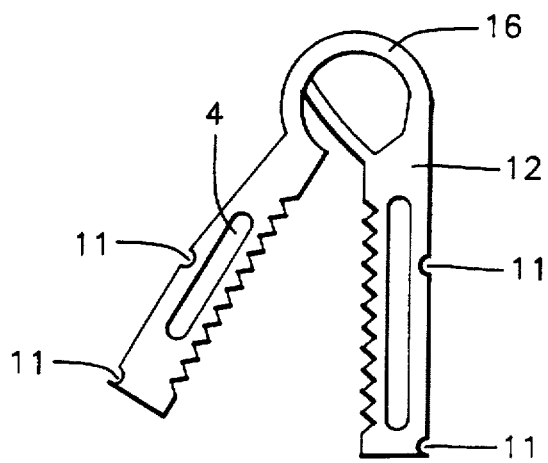
FIG. 5 is a side view of the second clamp in the open position.
Figure 6:
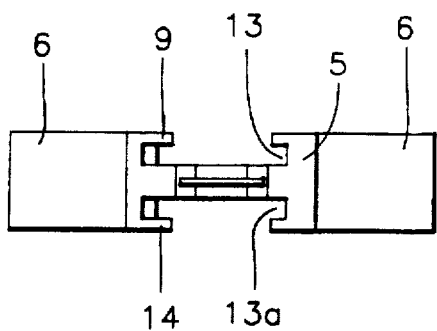
FIG. 6 is a side view of the holder seen from a bottom side.

The control clamp 1 has a contact part 3 (FIG. 4) which, when it is desired to use the second clamp 12, secures the latter in the same fixed position as the control clamp 1.

The second clamp 12 has recesses 11 which after shifting of the holder 5 to the closed position (FIG. 7) are placed opposite to the projections 9 on the holder. In this position it is possible to release the second clamp 12 from the holder 5.

In its closed position the second clamp 12 is locked to the object by the catch 15.

Both clamps have recesses 4 in their longitudinal direction which secure that deformations caused by squeezing will take place in these recesses.

The umbilical cored is inserted in the opening between clamps 1 and 12 (FIG. 1).

The control claim 1 has a control part 2 which is used as a counter pressure part when the holder 5 is shifted with two fingers on the control tabs 6.

Figure 7:
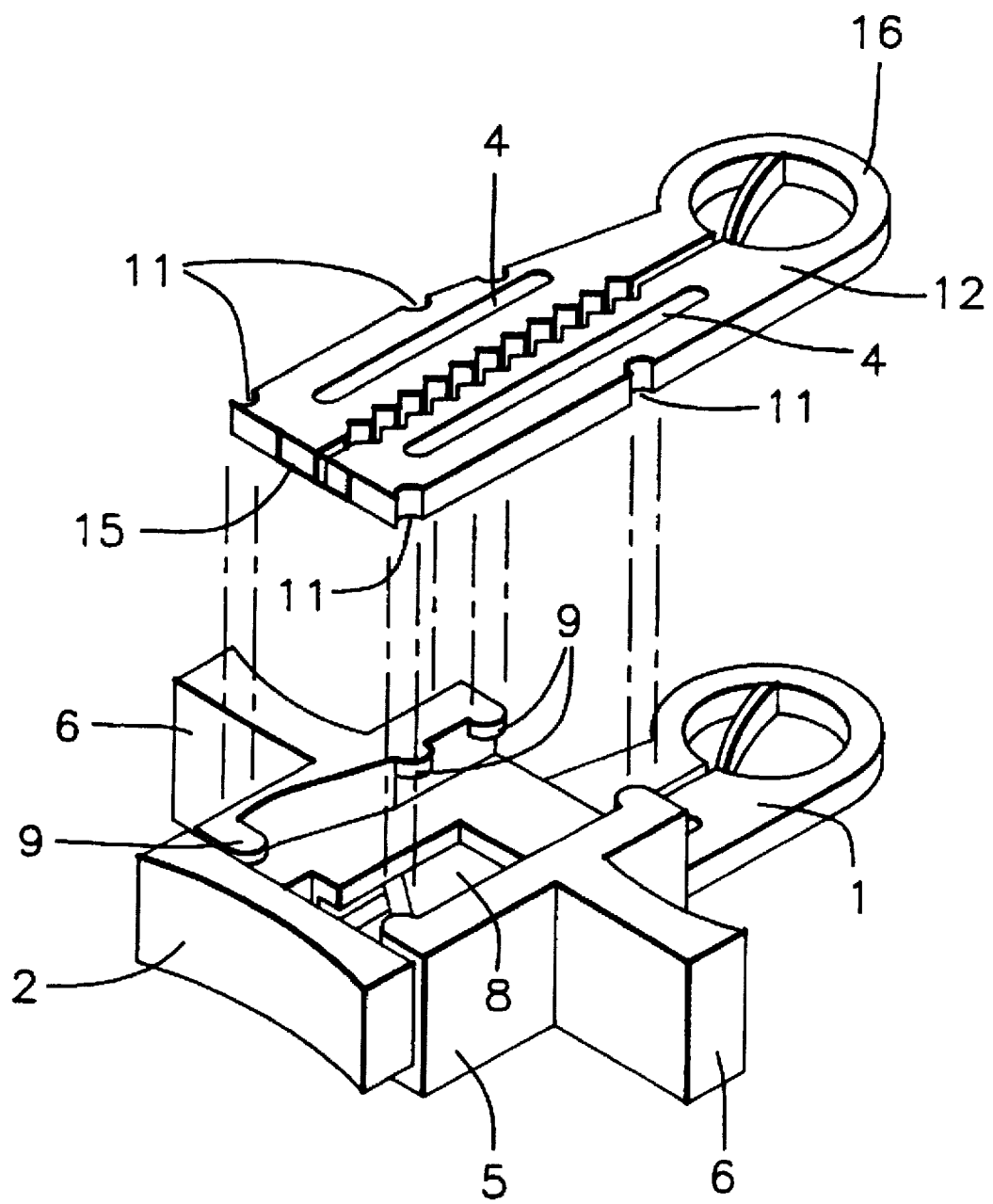
FIG. 7 is a perspective of the disposable safety squeezing device in the closed position, with one clamp released after the umbilical cord has been cut.

The umbilical cord is squeezed during the first stage of shifting. Further shifting brings the inclined knife 8 of the holder into contact with the umbilical cord which is then cut (FIG. 7). After cutting, the control clamp 1 continues to squeeze one part of the umbilical cord. For releasing this part of the umbilical cord, the holder 5 just has to be shifted in the opposite direction.

When released from the holder 5, the second clamp 12 remains locked in the closed position by the catch 15 and is release by cutting the spring bow 16 of the clamp.

We claim:

1. A device for squeezing and cutting an umbilical cord, said device comprising:

a control clamp having two legs, said two legs being interconnected at a hinge end by a hinge and having free ends at the opposite end, said free ends defining an opening therebetween, one of said two legs including a control part at the free end thereof, a second clamp having two legs, said two legs of said second clamp being interconnected at a hinge end by a hinge and having free ends at the opposite end, said free ends defining an opening therebetween, and said two legs including at the free ends a catch for mutually locking said two legs in a fixed abutment position, and a holder having two opposite wall members, each of said two opposite wall members being provided with two recesses for slidably receiving said two legs of the control clamp and said two legs of the second clamp, respectively, said holder further having a partition wall carrying a knife, said partition wall joining said two opposite wall members, and said knife protruding in one direction from said partition wall into a first interior part of the holder, said partition wall and said knife being arranged in parallel with a longitudinal plane of two recesses and so positioned as to enable the two legs of the control clamp and the two legs of the second clamp to pass on opposite sides of the knife while sliding in their respective recesses and the separation between said opposite wall members being just sufficient to allow the legs of the control clamp and the legs of the second clamp to slide in their respective recesses when the free ends of said legs of each said clamp are squeezed together, wherein squeezing and cutting of the umbilical cord is performed by slidably inserting the hinge ends of the legs of the control clamp and the second clamp into the recesses, respectively, in the first interior part of the holder, inserting the umbilical cord in the opening between the two legs of the control clamp and the second clamp, and pressing together the holder and the control part at the control clamp, pushing the control clamp and the second clamp through the recesses, respectively, to first squeeze the umbilical cord between the legs and subsequently cut the umbilical cord, while passing the partition wall and the knife.

2. A device according to claim 1, wherein a tab area of the holder includes one outwardly projecting control tab at each of said two opposite wall members.

3. A device according to claim 1, wherein the two legs of the second clamp include recesses, and one of said two recesses of one of said opposite wall members is bounded by projections corresponding to said recesses of said legs of the second clamp.

4. A device according to claim 3, wherein slots are located extending in a longitudinal direction of the two legs of the control clamp and the second clamp.

5. A device for squeezing and cutting an umbilical cord, said device comprising:

a clamp having two legs interconnected by a hinge, free ends of said legs being spaced apart and yieldably movable towards each other while compressing the clamp, a holder including recesses for supporting said two legs of said clamp, a knife and a tab area for bringing the holder from a first inactive position to a second position, in which the free ends of said legs are brought into mutual engagement, and the umbilical cord is squeezed and cut, the holder including two opposite wall members being arranged, in the first inactive position and in the second position, substantially in parallel and being joined by a partition wall carrying the knife, each of said opposite wall members being provided with at least one throughgoing bore, so that a distance between the at least one throughgoing bore in each of said opposite wall members corresponds substantially to a maximum width of the clamp when compressed, so as to enable the holder to be slidably shifted on said clamp from the first inactive position at the hinge to the second position at the free ends of the legs thereof.

6. A device according to claim 5, wherein there are two sets of throughgoing bores.

7. A device according to claim 6, wherein the tab area of the holder includes one outwardly projecting control tab at each of said opposite wall members.

8. A method for squeezing and cutting an umbilical cord, said method comprising the following steps:

placing the umbilical cord between two legs of at least one clamp, and shifting a knife carrying holder along said clamp, from a first inactive position to a second position, in which free ends of said two legs of said clamp are brought into mutual engagement, the umbilical cord thereby, in one single shifting step, being squeezed and cut, the knife carrying holder including a partition wall carrying a knife and the partition wall joining two opposite wall members slidingly receiving the two legs of the at least one clamp.

9. A method for squeezing and cutting an umbilical cord, said method comprising the following steps:

placing the umbilical cord between two legs of at least one clamp, said two legs being interconnected by a hinge, free ends of said legs being in a normal spaced apart position and yieldably movable towards each other while compressing the at least one clamp, and shifting a holder having two opposite wall members arranged substantially in parallel and joined by a partition wall carrying a knife with each of said opposite wall members being provided with at least one throughgoing bore so that a distance between the at least one throughgoing bore in each of said opposite wall members corresponds substantially to a maximum width of the at least one clamp when compressed, so as to enable the holder to be slidably shifted on said clamp from a first inactive position at the hinge to a second position at the free ends of the legs thereof so that the free ends of said legs are brought into mutual engagement, and the umbilical cord is squeezed and cut.

10. A holder for squeezing and cutting an umbilical cord by use of a control clamp having two legs, said two legs being interconnected at a hinge end by a hinge and having free ends at the opposite end, said free ends defining an opening therebetween, one of said two legs including a control part at the free end thereof, and a second clamp having two legs, said two legs being interconnected at a hinge end by a hinge and having free ends at the opposite end, said free ends defining an opening therebetween, and said two legs including at the free ends a catch for mutually locking said two legs in a fixed abutment position, said holder comprising:

two opposite wall members, each of said two opposite wall members being provided with two recesses for slidably receiving the two legs of the control clamp and the two legs of the second clamp, respectively, and a partition wall carrying a knife, said partition wall joining said two opposite wall members, and said knife protruding in one direction from said partition wall into a first interior part of the holder, said partition wall and said knife being arranged in parallel with a longitudinal plane of said two recesses and so positioned as to enable the two legs of the control clamp and the two legs of the second clamp to pass on opposite sides of the knife while sliding in their respective recesses and the separation between said opposite wall members being just sufficient to allow the legs of the control clamp and the legs of the second clamp to slide in their respective recesses when the free ends of said legs of each said clamp are squeezed together, wherein squeezing and cutting of the umbilical cord is performed by slidably inserting the hinge ends of the legs of the control clamp and the second clamp into the recesses, respectively, in the first interior part of the holder, inserting the umbilical cord in the opening between the two legs of the control clamp and the second clamp, and pressing together the holder and the control part at the control clamp, pushing the control clamp and the second clamp through the recesses, respectively, to first squeeze the umbilical cord between the legs and subsequently cut the umbilical cord, while passing the partition wall and the knife.

\* \* \* \* \*